(12) United States Patent
Stevens et al.

(10) Patent No.: US 9,302,951 B2
(45) Date of Patent: Apr. 5, 2016

(54) IONIC LIQUID ALKYLATION OF 1-BUTENE TO PRODUCE 2,5-DIMETHYLHEXANE

(71) Applicant: UOP LLC, Des Plaines, IL (US)

(72) Inventors: Carl J. Stevens, Lake Forest, IL (US); Susie C. Martins, Carol Stream, IL (US); Paul T. Barger, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 268 days.

(21) Appl. No.: 14/169,059

(22) Filed: Jan. 30, 2014

(65) Prior Publication Data

US 2015/0210609 A1 Jul. 30, 2015

(51) Int. Cl.
*C07C 2/58* (2006.01)
*C07C 2/60* (2006.01)
*C07C 2/62* (2006.01)
*C07C 5/367* (2006.01)
*C07C 5/41* (2006.01)
*C07C 5/27* (2006.01)

(52) U.S. Cl.
CPC .............. *C07C 2/60* (2013.01); *C07C 5/2751* (2013.01); *C07C 5/41* (2013.01); *C07C 2527/125* (2013.01)

(58) Field of Classification Search
CPC .............. C07C 2/58; C07C 2/60; C07C 2/62; C07C 5/367
USPC .................. 585/725, 722, 728, 418, 407, 322
See application file for complete search history.

(56) References Cited

U.S. PATENT DOCUMENTS

| | | | |
|---|---|---|---|
| 7,432,408 B2 | 10/2008 | Timken et al. | |
| 8,183,425 B2 | 5/2012 | Luo et al. | |
| 8,198,494 B2 | 6/2012 | Elomari et al. | |
| 2003/0004381 A1 | 1/2003 | Feng et al. | |
| 2008/0146858 A1* | 6/2008 | Elomari ................... C07C 2/58 585/331 |
| 2008/0287719 A1 | 11/2008 | Jan et al. | |
| 2008/0312482 A1 | 12/2008 | Jan et al. | |
| 2012/0283500 A1 | 11/2012 | Liu et al. | |

FOREIGN PATENT DOCUMENTS

| | | |
|---|---|---|
| EP | 1310472 A1 | 5/2003 |
| EP | 2235137 | 7/2009 |
| JP | 2004161763 A | 6/2004 |
| WO | WO 2009/085449 A1 | 7/2009 |

OTHER PUBLICATIONS

Search Report dated May 6, 2015 for corresponding PCT Appln. No. PCT/US2015/012820.
Bui et al., "Alkylation using ionic liquids as catalysts," Green Chemistry (2009), 11(12), 1917-2064.
Tang et al., "Improved 1-butene/isobutane alkylation with ionic liquids and tunable . . . ," Journal of Catalysis (2009), vol. 268, 243-250.
Cui et al., "Ionic liquid enhanced alkylation of iso-butane and 1-butene," Catalysis Today (2013), vol. 200, 30-35.
Xing et al., "Isobutane alkylation using acidic ionic liquid catalysts," Catalysis Communications (2012), vol. 26, 68-71.

* cited by examiner

*Primary Examiner* — Thuan D Dang

(57) ABSTRACT

A process for producing dimethylhexanes (DMH) is provided. The DMH can be used to produce p-xylene. The process involves the alkylation of isobutane and 1-butene using an ionic liquid to produce naphtha that is rich in DMH. The DMH is then converted in high selectivity to xylene, including p-xylene, by dehydrocyclization.

18 Claims, 1 Drawing Sheet

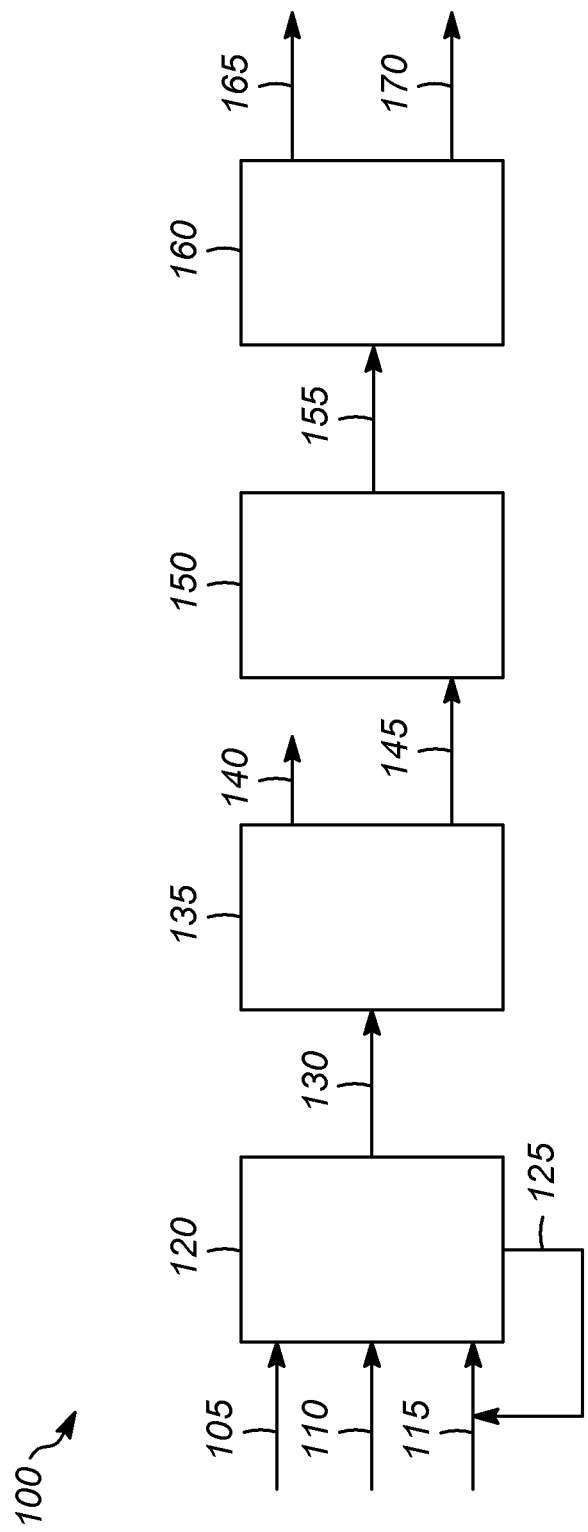

IONIC LIQUID ALKYLATION OF 1-BUTENE TO PRODUCE 2,5-DIMETHYLHEXANE

BACKGROUND OF THE INVENTION

P-xylene is typically made by reforming naphtha to reformate that is rich in $C_6$ to $C_{10}$ aromatics. The conversion of reformate to p-xylene is accomplished through a series of capital and energy intensive fractionations and reactions (primarily aromatics transalkylation and isomerization) along with selective isolation of p-xylene through simulated moving bed separation or crystallization.

There is a need for lower cost processes for making compounds that can be used to make xylenes and processes for making xylenes.

SUMMARY OF THE INVENTION

One aspect of the invention is a process for producing dimethylhexane. In one embodiment, the process includes introducing a stream comprising isobutane and a stream comprising 1-butene or a stream comprising isobutane and 1-butene to an alkylation reaction zone to form a reaction mixture, the stream comprising 1-butene or the stream comprising isobutane and 1-butene containing less than about 50 wt % total of 2-butene and isobutene; and alkylating the isobutane and the 1-butene in the alkylation reaction zone in the presence of a haloaluminate ionic liquid catalyst under alkylation conditions to form a stream rich in dimethylhexane, the stream rich in dimethylhexane having a ratio of dimethylhexane to trimethylpentane of at least about 2:1.

Another aspect of the invention is a process for producing xylenes. In one embodiment, the process includes introducing a stream comprising isobutane and a stream comprising 1-butene or a stream comprising isobutane and 1-butene to an alkylation reaction zone to form a reaction mixture, the stream comprising 1-butene or the stream comprising isobutane and 1-butene containing less than about 50 wt % total of 2-butene and isobutene; alkylating the isobutane and the 1-butene in the alkylation reaction zone in the presence of a haloaluminate ionic liquid catalyst under alkylation conditions to form a stream rich in dimethylhexane, the stream rich in dimethylhexane having a ratio of dimethylhexane to trimethylpentane of at least about 2:1; and dehydrocyclizing the stream rich in dimethylhexane in the presence of a dehydrocyclization catalyst under dehydrocyclization conditions to form a stream rich in xylenes.

BRIEF DESCRIPTION OF THE DRAWING

The FIGURE is an illustration of one embodiment of a process for making xylenes.

DETAILED DESCRIPTION OF THE INVENTION

Alkylation processes utilizing ionic liquids to make trimethylpentane (TMP) are known. For example, Tang et al., Improved 1-butene/isobutane alkylation with acidic ionic liquids and tunable acid/ionic liquid mixtures, J. of Catalysis 268, (2009) 243-250, describes a process for 1-butene/isobutane alkylation to yield $C_8$ alkylates using binary mixtures of certain acidic imidazolium ionic liquids and strong acids such as sulfuric acid or trifluoromethansulfonic acid. The trimethylpentane (TMP):dimethylhexane (DMH) selectivity was greater than 7 for ionic liquids where the acidity was imparted via the cation with sulfonic acid groups or the anion (hydrogen sulfate) or both. Thus, this process (and other similar processes) produces primarily TMP, not DMH.

The present invention involves a process for producing DMH. DMH can be used to produce xylenes, including p-xylene. The process involves the alkylation of isobutane and 1-butene using an ionic liquid to produce naphtha that is rich in DMH. In some embodiments, 30% or more of the DMH comprises 2,5-dimethylhexane (2,5-DMH). The 2,5-DMH is then converted in high selectivity to p-xylene by dehydrocyclization.

The increase in shale gas has made DMH made from n-butane and isobutane a lower cost feedstock than the typical naphtha feedstock currently used to produce p-xylene.

The FIGURE illustrates a process 100 for making xylenes. A stream containing 1-butene 105, a stream containing isobutane 110, and a stream containing ionic liquid catalyst 115 are fed to an ionic liquid alkylation reaction zone 120 under alkylation conditions. Alternatively, the feed can comprise a mixture of 1-butene and isobutane. For use in an alkylation process, it is not necessary to separate the 1-butene from other paraffins such as isobutane and n-butane.

The 1-butene and isobutane are alkylated, and the hydrocarbon phase containing DMH and the ionic liquid catalyst are allowed to separate. The separated ionic liquid 125 can be recycled to the alkylation reaction zone 120. The ionic liquid catalyst can be regenerated using known methods as needed.

A DMH enriched stream 130 exits the alkylation reaction zone 120. The DMH enriched stream 130 can optionally be sent to a separation zone 135 where it is separated into at least two streams, 140 and 145. In some embodiments, stream 145 is a stream enriched in 2,5-DMH, 2,4-DMH, or both and stream 140 contains the rest of the alkylation product. In other embodiments, there are at least three streams, with one stream being enriched in 2,5-DMH, one being enriched in 2,4-DMH, and the third containing the rest of the alkylated product. In some embodiments the separation zone 135 produces a isobutane stream which can be recycled to the reactor 120 and an n-butane stream, a C5 to C7 alkylate stream and optionally a C9+ alkylate leaving stream 145 enriched in 2,5 DMH. Other separations are possible, as would be understood by those of skill in the art.

Stream 145 is then sent to the dehydrocyclization zone 150 where it is converted to xylenes. Alternatively, DMH enriched stream 130 is sent directly to the dehydrocyclization zone 150.

Stream 155 which contains the xylenes can optionally be sent to a separation zone 160 where it can be separated into two or more streams containing xylene isomers 165 and 170.

To lower production costs, it will frequently be desirable to produce a $C_4$ stream that has 1-butene and butanes with the total of 2-butene and isobutene kept to a low level, for example, less than about 50 wt %, or less than about 40 wt %, or less than about 30 wt %, or less than about 20 wt %, or less than about 10 wt %, or less than about 5 wt %, or less than about 1 wt %.

Several methods are available for obtaining 1-butene. For example, a co-product stream from isobutylene consumption, which contains normal butenes and mixed butanes (Raff-2), can be fractionated to produce a stream that contains mostly 1-butene. Higher yields can be obtained by integrating a butene double bond isomerization catalyst with the fractionation. In this case, it is desirable to separate the $C_4$ olefins from the paraffins using extractive distillation. In place of the Raff-2 stream, it is possible to dehydrogenate or oxidatively dehydrogenate n-butane to form a stream that is rich in 1-butene. An alternative to lower temperature double bond isomerization coupled to fractionation is to recycle the 2-butene containing stream to the dehydrogenation/oxidehydrogenation reactor along with fresh n-butane to re-equilibrate the butene isomers. 1-Butene can also be obtained from the methanol to olefins (MTO) $C_4$ cut and separated by fractionation.

Typical alkylation reaction conditions include a temperature in the range of about −20° C. to about 100° C., or about −20° C. to about 70° C., or about 0° C. to about 70° C., or about 20° C. to about 70° C., or about 0° C. to about 60° C., or about 0° C. to about 50° C., or about 20° C. to about 60° C., or about 20° C. to about 50° C. It is preferred to have an ionic liquid that maintains its liquid state through the operating temperature range.

The pressure is typically in the range of atmospheric (0.101 MPa) to about 8.0 MPa, or about 0.300 MPa to about 2.5 MPa. The pressure is preferably sufficient to keep the reactants in the liquid phase.

The residence time of the reactants in the reaction zone is in the range of a few seconds to hours, or about 0.5 min to about 60 min, or about 5 min to about 60 min.

The molar ratio between isobutane and 1-butene is in the range of about 1:1 to about 50:1, or about 2:1 to about 50:1, or about 5:1 to about 30:1, or about 5:1 to about 25:1, or about 5:1 to about 20:1, or about 5:1 to about 15:1.

The catalyst is measured with respect to the amount of olefins, with a catalyst to olefin weight ratio between about 0.1:1 and about 10:1, or about 0.2:1 and about 5:1, or about 0.5:1 and 2:1.

Vigorous stirring is desirable to ensure good contact between the reactants and the catalyst.

In one embodiment, the ionic liquid and the isobutane are placed in the alkylation zone, and the 1-butene is added slowly at the reaction conditions. This provides low instantaneous olefin concentration, e.g., much greater than 100/1 isobutane/1-butene. It also provides shorter olefin residence time in the reactor, which favors the formation of DMH over TMP. In one embodiment with a continuous reactor, the stream containing 1-butene can be added at multiple injection locations to reduce the local concentration of olefin.

The alkylation reaction has high conversion of 1-butene, typically at least about 70%, or at least about 80%, or at least about 90%, or at least about 95%, or at least about 97%, or at least about 99%.

The ionic liquid comprises an organic cation and an anion. Suitable cations include, but are not limited to, nitrogen-containing cations and phosphorus-containing cations. Suitable organic cations include, but are not limited to:

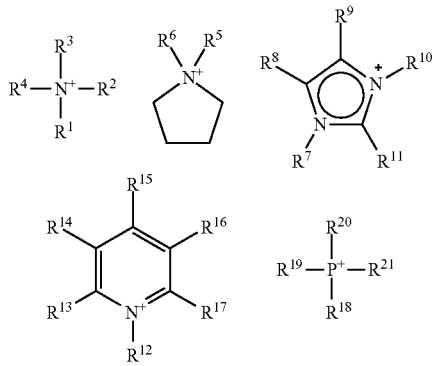

where $R^1$-$R^{21}$ are independently selected from $C_1$-$C_{20}$ hydrocarbons, $C_1$-$C_{20}$ hydrocarbon derivatives, halogens, and H.

Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable.

The anion can be derived from halides, sulfates, bisulfates, nitrates, sulfonates, fluoroalkanesulfonates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum, with the atom fraction of aluminum ranging from 0<Al<0.30 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3O_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$.

In some embodiments, the ionic liquid catalyst is a phosphonium based ionic liquid. In some embodiments, the anion of the ionic liquid is a haloaluminate, such as a chloroaluminate, or a bromoaluminate, or combinations thereof.

In some embodiments, the ionic liquid catalyst is combined with a Bronsted acid co-catalyst selected from the group consisting of HCl, HBr, HI and mixtures thereof, or compounds such as sec-butylchloride or tert-butylbromide that break down to form a hydrogen halide acid.

Due to the low solubility of hydrocarbons in ionic liquids, olefins-isoparaffins alkylation, like most reactions in ionic liquids, is generally biphasic and takes place at the interface in the liquid phase. The catalytic alkylation reaction is generally carried out in a liquid hydrocarbon phase, in a batch system, a semi-batch system or a continuous system using one reaction stage as is usual for aliphatic alkylation.

The heat generated by the reaction can be eliminated using any of the means known to the skilled person. At the reactor outlet, the hydrocarbon phase is separated from the ionic liquid phase by gravity settling based on density differences, or by other separation techniques known to those skilled in the art.

The alkylation product typically contains at least about 50 wt % $C_8$ compounds, or at least about 60 wt %, or at least about 70 wt %, or at least about 75 wt %. The $C_8$ fraction contains various isomers of DMH and TMP. The ratio of DMH:TMP is typically at least about 2:1, or at least about 3:1, or at least about 4:1, or at least about 5:1, or at least about 6:1, or at least about 7:1, or at least about 8:1, or at least about 9:1, or at least about 10:1, or at least about 15:1.

The alkylation product of 1-butene and isobutane is rich in DMH, including 2,3-DMH, 2,4-DMH, and 2,5-DMH. The alkylation product typically contains at least about 30 wt % DMH, at least about 40 wt % DMH, or at least about 50 wt % DMH, or at least about 60 wt % DMH. Of the total DMH, typically at least about 25 wt % is 2,5-DMH, or at least about 30 wt %, or at least about 35 wt %, or at least about 40 wt %. Of the total DMH, typically at least about 25 wt % is 2,4-DMH, or at least about 30 wt %, or at least about 35 wt %, or at least about 40 wt %.

The alkylation product rich in DMH can be separated into a stream rich in 2,5-DMH, a stream rich in 2,4-DMH, or both, if desired.

The amount of 2,5-DMH can be increased by isomerizing the 2,4-DMH to 2,5-DMH following separation of the 2,4-DMH.

The alkylation process of isobutane and 1-butene using an acidic ionic liquid catalyst provides a low cost source of DMH, and particularly, 2,5-DMH and 2,4-DMH.

In some embodiments, the entire alkylation product stream will be sent to the dehydrocyclization zone. Dehydrocyclization of the entire stream will produce a product rich in a mixture of xylenes. Alternatively, only a portion of the alkylation product stream, such as a stream rich in 2,5-DMH or a stream rich in 2,4 DMH, could be sent to the dehydrocyclization zone, which would produce a stream rich in p-xylene or m-xylene respectively.

In another embodiment, a C8 cut or C8+ cut can be sent to the dehydrocyclization reactor to simplify downstream separations. For example, if a C8 cut is used, then the amount of toluene produced in the dehydrocyclization reactor will be reduced significantly. The unreacted C8 alkylate can be separated from the xylenes with distillation. The close boiling point of toluene (b.p. 112° C.) to the boiling points of 2,5-DMH and 2,4 DMH (b.p. 109° C.) make it difficult to separate toluene from streams containing unreacted DMH. Small amounts of toluene can be removed via purge of the DMH containing stream. Likewise, removing a C9+ cut from the alkylate before sending the DMH containing stream 140 to the dehydrocyclization reactor reduces the amount of unreacted C9+ alkylate in stream 155 that must be removed from the xylenes.

Another advantage of the process is that the xylene mixture produced from the alkylation product rich in 2,5-DMH is enriched in p-xylene compared to an equilibrium mixture of xylenes which contains about 23% p-xylene. The alkylation product rich in 2,5-DMH can produce a xylene mixture with at least about 25% p-xylene, or at least about 30% p-xylene, or at least about 35% p-xylene, or at least about 40% p-xylene. This reduces separation costs.

For ease of discussion, the feed to the dehydrocyclization zone will be called a DMH rich stream, which includes the entire stream or a portion of the stream such as a stream rich in 2,5-DMH or a stream rich in 2,4 DMH.

Dehydrocyclization of the DMH rich stream can be performed at relatively low operating pressures. Operating conditions in a dehydrocyclization zone include a pressure of from about 100 kPa to 1.0 MPa (absolute), or about 100 to 500 kPa, or below about 300 kPa. Free hydrogen optionally is supplied to the process in an amount sufficient to correspond to a ratio of from about 0.1 to 10 moles of hydrogen per mole of hydrocarbon feedstock. By "free hydrogen" is meant molecular $H_2$, not combined in hydrocarbons or other compounds. Preferably, the reaction is carried out in the absence of added halogen. The volume of catalyst corresponds to a liquid hourly space velocity of from about 0.5 to 40 $hr^{-1}$. The operating temperature generally is in the range of about 260° C. to about 600° C.

The dehydrocyclization process produces an aromatics-rich effluent stream, with the aromatics content of the $C_{5+}$ portion of the effluent typically within the range of about 45 to 95 mass-%, and more usually more than about 85 mass-%. The composition of the aromatics depends principally on the feedstock composition and operating conditions, and comprises principally $C_6$-$C_{12}$ aromatics. $C_8$ aromatics are the principal aromatics produced from the DMH rich stream.

Paraffins and olefins in the DMH rich stream are converted selectively in the aromatization zone to the corresponding aromatics, i.e., most of the aromatics produced have the same number of carbon atoms as the paraffins or olefins from which they were converted. For example, DMH yields principally xylenes.

Although not wishing to be limited by theory, it is believed that the reaction proceeds principally by sequential dehydrogenation of paraffins to form olefins, diolefins (dienes), and trienes, followed by thermal cyclization. Specific paraffinic and olefinic isomers, representing individual paraffin isomers, thereby are converted to aromatic isomers without rearrangement.

The yield of the corresponding aromatic isomers, relative to the aromatized product which comprises the aromatic isomers, other aromatics and hydrocarbons lighter than the feedstock, is at least about 70 mass-%, preferably at least about 80 mass-%, and more preferably at least about 90 mass-%. DMH is aromatized to xylenes containing a relatively low proportion of ethylbenzene. p-Xylene is produced selectively from 2,5-DMH, and m-xylene is produced selectively from 2,4-DMH.

The dehydrocyclization zone comprises one or more reactors with provisions known in the art to adjust inlet temperatures to individual reactors. The DMH rich stream may contact the catalyst system in each of the respective reactors in upflow, downflow, or radial-flow mode. Since the preferred aromatization process operates at relatively low pressure, the low pressure drop in a radial-flow reactor favors the radial-flow mode. As the predominant dehydrocyclization and dehydrogenation reactions are endothermic, the reactor section generally will comprise two or more reactors with interheating between reactors to compensate for the endothermic heat of reaction and maintain dehydrocyclization conditions.

Using techniques and equipment known in the art, the aromatics-rich effluent usually is passed through a cooling zone to a disengaging zone. In the disengaging zone, typically maintained at about 0° C. to about 65° C., a hydrogen-rich gas is disengaged from a liquid phase. The resultant hydrogen-rich stream can then be recycled through suitable compressing means back to the first aromatization zone. The liquid phase from the disengaging zone is normally withdrawn and processed in a fractionating system in order to adjust the concentration of light hydrocarbons and produce an aromatics-rich effluent product.

The reactor section usually is associated with catalyst-regeneration options known to those of ordinary skill in the art, such as: (1) a semiregenerative unit containing fixed-bed reactors maintains operating severity by increasing temperature, eventually shutting the unit down for catalyst regeneration and reactivation; (2) a swing-reactor unit, in which individual fixed-bed reactors are serially isolated by manifolding arrangements as the catalyst become deactivated and the catalyst in the isolated reactor is regenerated and reactivated while the other reactors remain on-stream; (3) continuous regeneration of catalyst withdrawn from a moving-bed reactor, with reactivation and substitution of the reactivated catalyst, permitting higher operating severity by maintaining high catalyst activity through regeneration cycles of a few days; or: (4) a hybrid system with semiregenerative and continuous-regeneration provisions in the same unit. The preferred embodiment of the present invention is fixed-bed reactors in a semi-regenerative unit.

The dehydrocyclization catalyst can be any suitable dehydrocyclization catalyst.

One example of a suitable catalysts includes Pt or Cr on alkali-modified alumina or other non-acidic supports. When Pt is used, modifiers such as Sn, In, Re, Ga, Ce, or La, may be used to reduce undesired side-reactions, such as cracking, in favor of dehydrocyclization. These catalysts are described, for example, in U.S. Pat. No. 7,439,409, and Dehydrocyclization of Paraffins, J. of Catalysis, 23, 340-354 (1971), which are incorporated herein by reference.

In this embodiment, the catalyst preferably incorporates porous, adsorptive, high-surface-area materials. Within the scope of the present invention are refractory supports containing one or more of: (1) refractory inorganic oxides such as alumina, silica, titania, magnesia, zirconia, chromia, thoria, boria or mixtures thereof, (2) synthetically prepared or naturally occurring clays and silicates, which may be acid-treated; (3) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations; (4) spinels such as $MgAl_2O_4$, $FeAl_2O_4$, $ZnAl_2O_4$; and (5) combinations of materials from one or more of these groups.

Favored refractory inorganic oxides for use in the present invention comprise one or more of alumina, magnesia, titania, and zirconia, with alumina being particularly favored. Suitable alumina materials are the crystalline aluminas known as the theta-, alpha-, gamma-, and eta-alumina, with theta-, alpha-, and gamma-alumina giving favorable results and theta-alumina being particularly preferred. An especially favored catalyst comprises at least about 80 wt.-% theta alumina. Magnesia, alone or in combination with alumina, comprises an alternative inorganic-oxide component of the catalyst and provides the required nonacidity. The preferred refractory inorganic oxide will have an apparent bulk density of about 0.3 to about 1.1 g/cc and surface area characteristics such that the average pore diameter is about 20 to 1000 angstroms, the pore volume is about 0.05 to about 1 cc/g, and the surface area is about 50 to about 500 $m^2/g$.

It is essential that the catalyst be non-acidic, as acidity lowers the selectivity to para-xylene of the finished catalyst. The required nonacidity may be effected by any suitable method, including impregnation, co-impregnation with a platinum-group metal, or ion exchange. Impregnation of one or more of the alkali and alkaline earth metals, especially potassium, in a salt solution is favored as being an economically attractive method to neutralize the acidity of the support as well as to modify the hydrogenation metal. The alkali or alkaline earth metal effectively is associated with an anion such as hydroxide, nitrate or a halide such as chloride or bromide consistent with nonacidity of the finished catalyst, with a nitrate being favored. Optimally, the support is cold-rolled with an excess of solution in a rotary evaporator in an amount sufficient to provide a nonacidic catalyst. The alkali or alkaline earth metal may be coimpregnated along with a platinum-group metal component, as long as the platinum-group metal does not precipitate in the presence of the salt of the alkali or alkaline earth metal.

Ion exchange is an alternative method of incorporating nonacidity into the catalyst. The inorganic-oxide support is contacted with a solution containing an excess of metal ions over the amount needed to effect nonacidity. Although any suitable method of contacting may be used, an effective method is to circulate a salt solution over the support in a fixed-bed loading tank. A water-soluble metal salt of an alkali or alkaline earth metal is used to provide the required metal ions; a potassium salt is particularly preferred. The support is contacted with the solution suitably at a temperature ranging from about 10° C. to about 100° C. The nonacidity of the aromatization-catalyst support may be determined using a variety of methods known in the art. A preferred method of determining acidity is the heptene-cracking test: conversion of heptene, principally by cracking, isomerization and ring formation, is measured at specified conditions, with cracking being particularly indicative of the presence of strong acid sites.

An alternative suitable support having inherent nonacidity may be termed a "synthetic hydrotalcite" characterized as a layered double hydroxide or metal-oxide solid solution. Hydrotalcite is a clay with the ideal unit cell formula of $Mg_6Al_2(OH)_{16}(CO_3)4H_2O$, and closely related analogs with variable magnesium/aluminum ratios may be readily prepared. These embodiments are solid solutions of a divalent metal oxide and a trivalent metal oxide having the general formula $(M^{+2}_xO)(M^{+3}_yO)OH_y$, derived by calcination of synthetic hydrotalcite-like materials whose general formula may be expressed as $(M^{+2})_x(M^{+3})_y(OH)_zA_q.rH_2O$. $M^{+2}$ is divalent metal or combination of divalent metals selected from the group consisting of magnesium, calcium, barium, nickel, cobalt, iron, copper and zinc. $M^{+3}$ is a trivalent metal or combination of trivalent metals selected from the group consisting of aluminum, gallium, chromium, iron, and lanthanum. Both $M^{+2}$ and $M^{+3}$ may be mixtures of metals belonging to the respective class: for example, $M^{+2}$ may be pure nickel or may be both nickel and magnesium, or even nickel-magnesium-cobalt; $M^{+3}$ may be solely aluminum or a mixture of aluminum and chromium, or even a mixture of three trivalent metals such as aluminum, chromium, and gallium. $A_q$ is an anion, most usually carbonate although other anions may be employed equivalently, especially anions such as nitrate, sulfate, chloride, bromide, hydroxides, and chromate. The ratio x/y of the divalent and trivalent metals can vary between about 2 and about 20, with the ratios of 2 to about 10 being preferred. The case where $M^{+2}$ is magnesium, $M^{+3}$ is aluminum, and A is carbonate corresponds to the hydrotalcite series. Calcination of such layered double hydroxides results in destruction of the layered structure and formation of materials which are effectively described as solid solutions of the resulting metal oxides. It is preferable that the $(M^{+2}_xO)(M^{+3}_yO)OH_y$ solid solution has a surface area at least about 150 $m^2/g$, more preferably at least 200 $m^2/g$ and it is even more preferable that it be in the range from 300 to 350 $m^2/g$. Preparation of Suitable Basic Metal-Oxide Supports is Described in Detail in U.S. Pat. No. 5,254,743.

An inorganic-oxide powder may be formed into a suitable catalyst material according to any of the techniques known to those skilled in the catalyst-carrier-forming art. The favored form of the preferred non-zeolytic catalyst support is a sphere.

In an alternative embodiment, the aromatization catalyst comprises a non-acidic large-pore molecular sieve. Suitable molecular sieves generally have a maximum free channel diameter or "pore size" of Å or larger, and preferably have a moderately large pore size of about 7 to 8 Å, and materials containing a significant amount of external surface. Such molecular sieves include those characterized as LTL, BPH, OFF, MOR, MTW, FAU, AFI, BEA or MWW structure type by the IUPAC Commission on Zeolite Nomenclature, with the LTL structure being preferred. It is essential that the preferred L-zeolite be non-acidic, as acidity in the zeolite lowers the selectivity to aromatics of the finished catalyst. In order to be "non-acidic," the zeolite has substantially all of its cationic exchange sites occupied by nonhydrogen species. Preferably the cations occupying the exchangeable cation sites will comprise one or more of the alkali and alkaline earth metals, particularly Li, Na, K, Rb, Cs, Mg, Ca, Sr and Ba. Other cationic species may be present alternatively or in addition to the foregoing. An especially preferred nonacidic L-zeolite is potassium-form L-zeolite.

An essential ingredient of the aromatization catalyst is a metal component comprising at least one metal selected from Groups VIII (IUPAC 8-10) and IA of the Periodic Table, including the platinum-group metals, Fe, Co, Ni, Cu, Ag and Au. Of the preferred Group VIII platinum-group metals, i.e., platinum, palladium, rhodium, ruthenium, osmium and iridium, platinum is particularly preferred. Mixtures of platinum-group metals as a uniformly distributed component or platinum-group surface metals also are within the scope of this invention. The platinum-group metal component may exist within the final catalytic composite as a compound such as an oxide, sulfide, halide, or oxyhalide, in chemical combination with one or more of the other ingredients of the composite, or as an elemental metal. Best results are obtained when substantially all of the metals are present in the elemental state. The platinum-group metal component may be present in the final catalyst composite in any amount which is catalytically effective, but relatively small amounts are preferred. The uniformly distributed platinum-group metals generally will comprise from about 0.01 to 5 wt.-% of the final catalyst, and preferably about 0.05 to 2 wt.-%, calculated on an elemental basis.

The aromatization catalyst may contain a halogen component. The halogen component may be either fluorine, chlorine, bromine or iodine or mixtures thereof with chlorine being preferred. Considering the nonacidic nature of the support, the halogen usually is incorporated into the catalyst only in association with the incorporation of a metal component. The halogen component is generally present in a combined state with the inorganic-oxide support. The halogen component is preferably well distributed throughout the catalyst and may comprise from more than 0.2 to about 15 wt.-% calculated on an elemental basis, of the final catalyst.

It is within the scope of the present invention that the aromatization catalyst may contain supplemental metal components known to modify the effect of the preferred platinum component. Such metal modifiers may include one or more of the Group IVB (IUPAC 14) metals, Group 1b (IUPAC 11) metals, rhenium, indium, gallium, bismuth, zinc, uranium, thallium and the rare earth (lanthanide) metals. Group VIa (IUPAC 6) metals are disfavored, considering the known toxicity of chromium. One or more of tin, indium, germanium, gallium, copper, silver, gold, lead, zinc and the rare-earth elements are favored modifier metals, with tin, indium, germanium, cerium and lead being particularly favored. If present, the concentration of a metal modifier in the catalyst may be within the range of 0.001 to 5.0 wt.-%. Catalytically effective amounts of such metal modifiers may be incorporated into the catalyst by any means known in the art.

Another example of a dehydrocyclization catalyst is described in U.S. Pat. No. 6,177,601, which is incorporated herein by reference. In this embodiment, the catalyst is a large pore molecular sieve catalyst containing a uniformly distributed platinum-group metal component, and a tin component incorporated into the large pore molecular sieve by secondary synthesis.

The catalyst particles have a non-acidic large-pore molecular sieve. Suitable molecular sieves generally have a maximum free channel diameter or "pore size" of 6 Å or larger, and preferably have a moderately large pore size of about 7 to 8 Å. Such molecular sieves include, without so limiting the invention, those characterized as AFI, BEA, ERI, FAU, FER, LTL or MWW structure type by the IUPAC Commission on Zeolite Nomenclature; the LTL structure is preferred. It is essential that the preferred L-zeolite be non-acidic, as acidity in the zeolite lowers the selectivity to aromatics of the finished catalyst. In order to be "non-acidic," the zeolite has substantially all of its cationic exchange sites occupied by nonhydrogen species. Preferably the cations "A" occupying the exchangeable cation sites comprise one or more of the alkali and alkaline-earth metals, although other cationic species may be present. An especially preferred nonacidic L-zeolite is potassium-form L-zeolite.

The zeolite is typically combined with a binder in order to provide a convenient form for use in the catalyst particles of the present invention. The art teaches the suitability of a variety of refractory inorganic oxide binders. One or more of silica, alumina or magnesia are preferred binder materials of the present invention. One or both of amorphous silica and alumina are especially preferred. In one embodiment, excellent results are obtained when using a synthetic white silica powder precipitated as ultra-fine spherical particles from a water solution. A silica binder preferably is nonacidic, contains less than 0.3 mass-% sulfate salts, and has a BET surface area of from about 120 to 160 $m^2/g$.

The catalyst support may incorporate other porous, adsorptive, high-surface-area materials. Within the scope of the present invention are refractory supports containing one or more of: (1) refractory inorganic oxides such as alumina, silica, titania, magnesia, zirconia, chromia, thoria, boria or mixtures thereof, (2) synthetically prepared or naturally occurring clays and silicates; which may be acid-treated; (3) non-zeolitic molecular sieves, such as the aluminophosphates or silicoaluminophosphates of U.S. Pat. Nos. 4,310,440, 4,440,871 and 4,554,143, (4) spinels such as $MgAl_2O_4$, $FeAl_2O_4$, $ZnAl_2O_4$; and (5) combinations of materials from one or more of these groups.

An alkali-metal component is a highly preferred constituent of the dehydrocyclization catalyst particles. One or more of the alkali metals, including lithium, sodium, potassium, rubidium, cesium and mixtures thereof, may be used, with potassium being preferred. The alkali metal optimally will occupy essentially all of the cationic exchangeable sites of the non-acidic L-zeolite as described hereinabove.

Of the Group VIII platinum-group noble metals, i.e., platinum, palladium, rhodium, ruthenium, osmium and iridium, platinum is preferred. Mixtures of platinum-group metals also are within the scope of this invention, but it is preferred that the platinum-group metal component consists essentially of a platinum component. The platinum-group metal component may exist within the final catalytic composite as a compound such as an oxide, sulfide, halide, or oxyhalide, in chemical combination with one or more of the other ingredients of the composite, or as an elemental metal. Best results are obtained when substantially all of the metals are present in the elemental state. The platinum-group metal component may be present in the final catalyst composite in any amount which is catalytically effective, but relatively small amounts are preferred. The uniformly distributed platinum-group metals generally will comprise from about 0.01 to 5 mass-% of the final catalyst, and preferably about 0.05 to 2 mass-%, calculated on an elemental basis.

The catalyst may contain other metal components known to modify the effect of the platinum-group-metal component. Such metal modifiers may include but are not limited to tin, rhenium, gallium, manganese, zinc, uranium, dysprosium, thallium and mixtures thereof. Catalytically effective amounts of such metal modifiers may be incorporated into the catalyst by any means known in the art. Generally an optional metal modifier is present in a concentration of from about 0.01 to 5 mass-% of the finished catalyst on an elemental basis. The ratio of tin to platinum in the finished catalyst affects catalyst performance, particularly conversion of par-affinic hydrocarbons at a given set of operating conditions. The Sn/Pt mass ratio preferably is above about 1.5, and more preferably at least about 2; in some cases, a ratio of 3 or more is advantageous.

The dehydrocyclization catalyst may contain a halogen component, although the catalyst preferably has the essential absence of halogen. An optional halogen component may be fluorine, chlorine, bromine or iodine or mixtures thereof with chlorine being preferred. Considering the nonacidic nature of the support, such halogen usually is incorporated into the catalyst only in association with the incorporation of a metal component. An optional halogen component is generally present in a combined state with the inorganic-oxide support, and preferably is well distributed throughout the catalyst and may comprise from more than 0.2 to about 15 mass-% calculated on an elemental basis, of the final catalyst.

The process typically includes an aromatics-rich-product separation zone for separation of the aromatics formed in the reaction. The separation zone generally comprises either solvent extraction, adsorptive separation or a combination of solvent extraction and adsorptive separation in sequence to separate the products into a low-octane paraffin fraction and an aromatic-rich fraction. Solvent extraction separates essentially all of the paraffins and olefins, as well as the relatively smaller amounts of naphthenes, from an aromatic concentrate. Adsorptive separation selectively separates classes of paraffin and olefin isomers, depending on the adsorbent and operating conditions, with selected degrees of branching. Solvent extraction thus produces a concentrated aromatics stream, corresponding approximately to the aromatized product, and a concentrated aliphatic stream containing essentially all of the paraffins and olefins; in contrast, adsorptive separation generally produces a mixed aromatic-aliphatic stream and an aliphatic stream containing straight-chain and optionally lower-branched paraffins and olefins.

The separation zone yields an aromatics concentrate and an aliphatic concentrate. The aliphatic concentrate comprises paraffins and olefins unconverted in the aromatization reaction as well as olefins and other unsaturates formed in the reaction. This stream preferably is recycled for further conversion over the dehydrocyclization catalyst to increase the yield of aromatics.

Example 1

Preparation of Tributylhexylphosphonium Chloroaluminate Ionic Liquid

Tributylhexylphosphonium chloroaluminate is a room temperature ionic liquid prepared by mixing anhydrous tributylhexylphosphonium chloride with slow addition of 2 moles of anhydrous aluminum chloride in an inert atmosphere. After several hours of mixing, a pale yellow liquid is obtained. The resulting acidic IL was used in the following examples.

Example 2

Alkylation of Isobutane with 1-Butene Using Tributylhexylphosphonium Chloroaluminate Ionic Liquid Catalyst Alkylation of isobutane with 1-butene was carried out in a 300 cc continuously stirred autoclave. 8 grams of tributylhexylphosphonium heptachloroaluminate (TBHP)-$Al_2Cl_7$ ionic liquid was added to the autoclave in a glovebox to avoid exposure to moisture. 80 grams of isobutane were then charged, and the autoclave was pressured to 500 psig with nitrogen. Stirring was started at 1900 rpm. 6.5 grams of olefin feed (1-butene feed to which 10% n-pentane tracer had been added) was then charged into the autoclave at an olefin feed rate of 7.79 mL olefin/hour until the target isobutane to olefin (i/o) molar ratio of 10:1 was reached (about 2 hours). Stirring was stopped, and the ionic liquid and hydrocarbon phases were allowed to settle for 30 seconds. The hydrocarbon phase was then analyzed by GC. For this example, the autoclave temperature was maintained at 25° C. In these 2 hours, the selectivity to $C_8$s was 82%, of which 83% were dimethylhexanes. The ratio of 2,5-dimethylhexane to 2,4-dimethylhexane to 2,3-dimethylhexane and 2,2-dimethylhexane was 65.7:60.1:23.6:1. The results are shown in Table 1.

Example 3

Alkylation of Isobutane with 1-Butene Using Tributylhexylphosphonium Chloroaluminate Ionic Liquid Catalyst Alkylation of isobutane with 1-butene was carried out in a 300 cc continuously stirred autoclave. 8 grams of tributylhexylphosphonium heptachloroaluminate (TBHP)-$Al_2Cl_7$ ionic liquid was added to the autoclave in a glovebox to avoid exposure to moisture. 80 grams of isobutane were then charged, and the autoclave was pressured to 500 psig with nitrogen. Stirring was started at 1900 rpm. 8.5 grams of olefin feed (1-butene feed to which 10% n-pentane tracer had been added) was then charged into the autoclave at an olefin feed rate of 7.79 mL olefin/hour for 30 minutes. Stirring was stopped, and the ionic liquid and hydrocarbon phases were allowed to settle for 30 seconds. The hydrocarbon phase was then analyzed by GC. Olefin addition was resumed at a rate of 7.79 mL olefin/hour for another 30 minutes. Again the phases were allowed to separate before sampling by GC. This procedure was repeated another 3 times for a total olefin addition time of 2.5 hours, after which olefin addition was stopped, but the reactor contents were allowed to continue stirring for one additional hour. After phase separation, one final GC analysis was collected. For this example, the autoclave temperature was maintained at 25° C. In the 3.5 hours, the selectivity to $C_8$s was 78%, of which 83% were dimethylhexanes. The ratio of 2,5-dimethylhexane to 2,4-dimethylhexane to 2,3-dimethylhexane, and 2,2-dimethylhexane was 48.1:43.8:17.1:1. The results are shown in Table 1.

Example 4

Isomerization of 2,4-Dimethylhexane Using Tributylhexylphosphonium Chloroaluminate Ionic Liquid Catalyst Isomerization of 2,4-dimethylhexane was carried out in a 300 cc continuously stirred autoclave. 8 grams of tributylhexylphosphonium heptachloroaluminate (TBHP)-$Al_2Cl_7$ ionic liquid was added to the autoclave in a glovebox to avoid exposure to moisture along with 1.13 g of 2.4-dimethylhexane. 80 grams of isobutane were then charged, and the autoclave was pressured to 500 psig with nitrogen. Stirring was started at 1900 rpm and was continued for 30 minutes. The mixing was then stopped, and the ionic liquid and hydrocarbon phases were allowed to settle for 30 seconds. The hydrocarbon phase was then analyzed by GC. Stirring was resumed for another 30 minutes. Again the phases were allowed to separate before sampling by GC. This procedure was repeated another 3 times for mixing time of 3.5 hours. For this example, the autoclave temperature was maintained at 25° C. In the 3.5 hours, 63% of the 2.4-dimethylhexane was isomerized to 2,5-dimethylhexane with 43% selectivity.

TABLE 1

|  | Example 2 | Example 3 | Example 4 |
|---|---|---|---|
|  | $C_{5+}$ Product Distribution wt % | | |
| $iC_5$ | 2.91 | 3.79 | 4.32 |
| $C_6s$ | 2.46 | 2.88 | 2.26 |
| $C_7s$ | 2.46 | 2.97 | 3.85 |
| 224 TMP | 3.73 | 3.30 | 0.85 |
| 233 TMP | 1.06 | 0.94 | 0.46 |
| 234 TMP | 0.61 | 0.54 | 0.17 |
| 22 DMH | 0.45 | 0.59 | 0.26 |
| 23 DMH | 10.61 | 10.08 | 9.04 |
| 24 DMH | 27.04 | 25.97 | 37.24 |
| 25 DMH | 29.58 | 28.35 | 27.06 |
| Other $C_8s$ | 8.74 | 8.49 | 9.08 |
| $C_{9+}$ | 10.35 | 12.17 | 4.39 |

Example 5

Dehydrocyclization of a DMH-Enriched Alkylation Product to Xylenes

The alkylation product of Example 2 can be fractionated to separate the desired C8 components from any C7− and C9+ by-products. The fractionated C8 stream will contain about 13 wt % 33 wt % 24-DMH and 36% 25-DMH. Dehydrocyclization of this stream over a fixed-bed Pt/Sn/K/Al2O3 catalyst at 540° C., 15 psig, 0.5 hr-1 WHSV with an $H_2$ co-feed (3.3:1 $H_2$:hydrocarbon molar ratio) is expected to produce a reactor effluent containing at least 50 wt % xylenes with 44% p-xylene in the total xylenes. The reactor effluent can be fractionated to remove undesired by-products and afford a xylene stream suitable for further separation into pure xylene isomers. This xylene stream is significantly enriched in p-xylene compared with the 23% p-xylene found in typical refinery xylene streams produced by reforming or methylaromatic transalkylation.

While at least one exemplary embodiment has been presented in the foregoing detailed description of the invention, it should be appreciated that a vast number of variations exist. It should be also appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for producing dimethylhexane comprising:
   introducing a stream comprising isobutane and a stream comprising 1-butene or a stream comprising isobutane and 1-butene to an alkylation reaction zone to form a reaction mixture, the stream comprising 1-butene or the stream comprising isobutane and 1-butene containing less than about 50 wt % total of 2-butene and isobutene; and
   alkylating the isobutane and the 1-butene in the alkylation reaction zone in the presence of a haloaluminate ionic liquid catalyst wherein the haloaluminate ionic liquid catalyst comprises a cation selected from one or more of

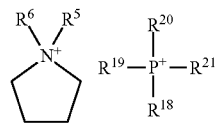

where $R^5$, $R^6$, $R^{18-21}$ are independently selected from $C_1$-$C_{20}$ hydrocarbons, $C_1$-$C_{20}$ hydrocarbon derivatives, halogens, and H;
   under alkylation conditions to form a stream rich in dimethylhexane, the stream rich in dimethylhexane having a ratio of dimethylhexane to trimethylpentane of at least about 2:1.

2. The process of claim 1 wherein the haloaluminate ionic liquid catalyst comprises a chloroaluminate ionic liquid catalyst, a bromoaluminate ionic liquid catalyst, or combinations thereof.

3. The process of claim 1 wherein the stream rich in dimethylhexane comprises at least about 25 wt % 2,5-dimethylhexane based on a total weight of dimethylhexane, or at least about 25 wt % 2,4-dimethylhexane based on a total weight of dimethylhexane, or both.

4. The process of claim 1 wherein a ratio of isobutane to 1-butene is in a range of about 1:1 to about 50:1.

5. The process of claim 1 wherein the alkylation conditions include a temperature in a range of about −20° C. to about 100° C., and a pressure in a range of about 0.101 MPa to about 8.0 MPa.

6. The process of claim 1 wherein a ratio of catalyst to olefins is in a range of about 0.1:1 to about 10:1.

7. The process of claim 1 further comprising stirring the reaction mixture and the acidic ionic liquid catalyst.

8. The process of claim 1 further comprising dehydrocyclizing the stream rich in dimethylhexane in the presence of a dehydrocyclization catalyst under dehydrocyclization conditions to form a stream rich in xylenes.

9. The process of claim 1 further comprising:
   separating the stream rich in dimethylhexane into a stream rich in 2,5-dimethylhexane and a residual stream; and
   dehydrocyclizing the stream rich in 2,5-dimethylhexane in the presence of a dehydrocyclization catalyst under dehydrocyclization conditions to form a stream rich in p-xylene.

10. The process of claim 1 further comprising:
    separating the stream rich in dimethylhexane into a stream rich in 2,4-dimethylhexane and a residual stream; and
    dehydrocyclizing the stream rich in 2,4-dimethylhexane in the presence of a dehydrocyclization catalyst under dehydrocyclization conditions to form a stream rich in m-xylene.

11. The process of claim 1 further comprising isomerizing the stream rich in dimethylhexane in the presence of an isomerization catalyst under isomerization conditions to convert a portion of 2,4-dimethylhexane to 2,5-dimethylhexane.

12. A process for producing xylenes comprising:
    introducing a stream comprising isobutane and a stream comprising 1-butene or a stream comprising isobutane and 1-butene to an alkylation reaction zone to form a reaction mixture, the stream comprising 1-butene or the stream comprising isobutane and 1-butene containing less than about 50 wt % total of 2-butene and isobutene;
    alkylating the isobutane and the 1-butene in the alkylation reaction zone in the presence of a haloaluminate ionic liquid catalyst wherein the haloaluminate ionic liquid catalyst comprises a cation selected from one or more of

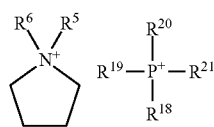

where $R^5$, $R^6$, $R^{18-21}$ are independently selected from $C_1$-$C_{20}$ hydrocarbons, $C_1$-$C_{20}$ hydrocarbon derivatives, halogens, and H;

under alkylation conditions to form a stream rich in dimethylhexane, the stream rich in dimethylhexane having a ratio of dimethylhexane to trimethylpentane of at least about 2:1; and dehydrocyclizing the stream rich in dimethylhexane in the presence of a dehydrocyclization catalyst under dehydrocyclization conditions to form a stream rich in xylenes.

13. The process of claim 12 wherein the stream rich in dimethylhexane comprises at least about 25 wt % 2,5-dimethylhexane based on a total weight of dimethylhexane, or at least about 25 wt % 2,4-dimethylhexane based on a total weight of dimethylhexane, or both.

14. The process of claim 12 wherein a ratio of isobutane to 1-butene is in a range of about 1:1 to about 50:1.

15. The process of claim 12 wherein a ratio of catalyst to olefins is in a range of about 0.1:1 to about 10:1.

16. The process of claim 12 further comprising:
separating the stream rich in dimethylhexane into a stream rich in 2,5-dimethylhexane and a residual stream, and wherein dehydrocyclizing the stream rich in dimethylhexane comprises dehydrocyclizing the stream rich in 2,5-dimethylhexane to form a stream rich in p-xylene.

17. The process of claim 12 further comprising:
separating the stream rich in dimethylhexane into a stream rich in 2,4-dimethylhexane and a residual stream; and wherein dehydrocyclizing the stream rich in dimethylhexane comprises dehydrocyclizing the stream rich in 2,4-dimethylhexane to form a stream rich in m-xylene.

18. The process of claim 12 further comprising isomerizing the stream rich in dimethylhexane in the presence of an isomerization catalyst under isomerization conditions to convert a portion of 2,4-dimethylhexane to 2,5-dimethylhexane.

* * * * *